United States Patent
Charlton et al.

(10) Patent No.: US 11,253,467 B2
(45) Date of Patent: Feb. 22, 2022

(54) WRINKLE TREATMENT

(71) Applicant: SLC Skin LLC, Burbank, CA (US)

(72) Inventors: Stacy Lynn Charlton, Burbank, CA (US); Gary S. Huvard, Richmond, VA (US); Maura Fierro, Richmond, VA (US)

(73) Assignee: SLC Skin LLC., Burbank, CA (US)

( * ) Notice: Subject to any disclaimer, the term of this patent is extended or adjusted under 35 U.S.C. 154(b) by 0 days.

(21) Appl. No.: 16/702,265

(22) Filed: Dec. 3, 2019

(65) Prior Publication Data

US 2020/0170930 A1 Jun. 4, 2020

Related U.S. Application Data

(60) Provisional application No. 62/774,784, filed on Dec. 3, 2018.

(51) Int. Cl.
*A61K 8/9789* (2017.01)
*A61Q 19/08* (2006.01)

(52) U.S. Cl.
CPC ............ *A61K 8/9789* (2017.08); *A61Q 19/08* (2013.01)

(58) Field of Classification Search
CPC .............................. A61K 8/9789; A61Q 19/08
See application file for complete search history.

(56) References Cited

U.S. PATENT DOCUMENTS

| 2004/0131660 A1 | 7/2004 | Lange |
| 2004/0180101 A1* | 9/2004 | Dreyer .................. A61K 36/30 424/725 |
| 2004/0185123 A1 | 9/2004 | Mazzio |
| 2007/0003502 A1 | 6/2007 | Tanabe |
| 2007/0218145 A1 | 9/2007 | Gross |
| 2009/0041875 A1 | 2/2009 | Takada |
| 2009/0253666 A1 | 10/2009 | Lintner |
| 2010/0035831 A1 | 2/2010 | Matsunaga |
| 2013/0216596 A1 | 8/2013 | Petit |
| 2015/0342854 A1 | 12/2015 | Shibuya |
| 2016/0235796 A1* | 8/2016 | Kennedy .............. A61K 9/0014 |
| 2017/0135950 A1 | 5/2017 | Najafi |

(Continued)

FOREIGN PATENT DOCUMENTS

| KR | 20120076168 | 7/2012 | |
| WO | 03/057122 | 7/2003 | |
| WO | WO-2004022034 A1 * | 3/2004 | ............. A61K 31/59 |

OTHER PUBLICATIONS

Usui et al. ("Identification of HSP70-inducing activity in Arnica montana extract and purification and characterization of HSP70-inducers", Journal of Dermatological Science 78 (2015) 67-75) (Year: 2015).*

(Continued)

*Primary Examiner* — Quanglong N Truong
(74) *Attorney, Agent, or Firm* — Jeffer Mangels Butler & Mitchell LLP; Brennan C. Swain, Esq.

(57) ABSTRACT

A method of preparing a skin treatment that includes preparing an extract of *Arnica montana* by mixing *Arnica montana* with ethyl alcohol, and filtering out the solids thereby resulting in liquid *Arnica montana* extract. In a first dilution, diluting the liquid *Arnica montana* extract with distilled water resulting in a first diluted *Arnica montana* extract. In a second dilution, diluting the first diluted *Arnica montana* extract with alkaline water resulting in a liquid skin treatment.

5 Claims, 1 Drawing Sheet

| | | Volume (L) | Mass (g) | Batch Size (gal) |
|---|---|---|---|---|
| EXTRACTION | Extraction, total amount | 2.84 | 2276 | 0.75 |
| | Ethanol | 2.82 | 2173.5 | |
| | DI water | 0.10 | 102.4 | |
| | Arnica (2 oz/gal) | | 42.0 | |
| DILUTION | Starting amount (from extraction) | 2.84 | 2276 | |
| | DI water | 1.90 | 1900 | |
| | Alkaline water | 3.49 | 3494 | |
| | Diluted extract (L, g & gal total) | 8.01 | 7670 | 2.1 |
| ADDITIVES | Hypromellose (2.5 wt%) | | 191.8 | |
| | Fragrance (1 wt%) | | 76.7 | |
| | Colorant (.004 g/72 g or ~56 ppm) | | 0.43 | |
| | Mass % ethanol after dilution = | 28.3% | | |
| | Final volume per 0.75 gal batch = | 8.28 | | 2.2 |
| | Bottle Size, Fluid Oz. = | 4 | | |
| Product: | Number of bottles for each 0.75 gal batch = | 69 | | |

| Fluid Properties and Conversions | | Units |
|---|---|---|
| Density of 95.5% ethanol/4.5% water (by mass) | 0.803 | g/mL |
| 1 gallon = | 3.78 | Liters |
| 1 Fluid Oz = | 30 | mL |
| 1 oz Arnica = | 28 | g |
| Density of diluted extract (40ABV+6:1) (28% by mass ethanoL) | 0.957 | g/mL |

(56) References Cited

U.S. PATENT DOCUMENTS

2017/0143608 A1    5/2017   Saeki
2017/0181937 A1    6/2017   Richard

OTHER PUBLICATIONS

Lievers ("Unravelling the confusion around arnica's herbal and homeopathic use", The Pharmaceutical Journal (vol. 275), Sep. 3, 2005, p. 289-291.). (Year: 2005).*
Hajime (JP2002212052A Machine English Translation) (Year: 2001).*
Gusakova, S.D., et al., Lipophilic Extracts in Phytotherapy and Phytocosmetics: Production and Biological Properties; Chemistry of Natral Compounds, vol. 34, No. 4, 1998.
Kapoor, V P, National Botanical Research Institute, Lucknow—226 001, Uttar Pradesh, India, Herbal Cosmetics for Skin and Hair care; vol. 4(4) Jul.-Aug. 2005; p. 311.

* cited by examiner

|  |  | Volume (L) | Mass (g) | Batch Size (gal) |
|---|---|---|---|---|
| EXTRACTION | Extraction, total amount | 2.84 | 2276 | 0.75 |
|  | Ethanol | 2.82 | 2173.5 |  |
|  | DI water | 0.10 | 102.4 |  |
|  | Arnica (2 oz/gal) |  | 42.0 |  |
|  |  |  |  |  |
| DILUTION | Starting amount (from extraction) | 2.84 | 2276 |  |
|  | DI water | 1.90 | 1900 |  |
|  | Alkaline water | 3.49 | 3494 |  |
|  |  |  |  |  |
|  | Diluted extract (L, g & gal total) | 8.01 | 7670 | 2.1 |
|  |  |  |  |  |
| ADDITIVES | Hypromellose (2.5 wt%) |  | 191.8 |  |
|  | Fragrance (1 wt%) |  | 76.7 |  |
|  | Colorant (.004 g/72 g or ~56 ppm) |  | 0.43 |  |
|  |  |  |  |  |
|  | Mass % ethanol after dilution = | 28.3% |  |  |
|  | Final volume per 0.75 gal batch = | 8.28 |  | 2.2 |
|  |  |  |  |  |
|  | Bottle Size, Fluid Oz. = | 4 |  |  |
| Product: | Number of bottles for each 0.75 gal batch = | 69 |  |  |

| Fluid Properties and Conversions |  | Units |
|---|---|---|
|  |  |  |
| Density of 95.5% ethanol/4.5% water (by mass) | 0.803 | g/mL |
| 1 gallon = | 3.78 | Liters |
| 1 Fluid Oz = | 30 | mL |
| 1 oz Arnica = | 28 | g |
| Density of diluted extract (40ABV+6:1) (28% by mass ethanoL) | 0.957 | g/mL |

WRINKLE TREATMENT

CROSS REFERENCE TO RELATED APPLICATIONS

This application is a continuation in part of U.S. Patent Application No. 62/774,784, filed Dec. 3, 2018, the entirety of which is incorporated by reference herein.

FIELD OF THE INVENTION

The present invention relates generally to an improved wrinkle treatment.

BACKGROUND OF THE INVENTION

People are always looking for ways to combat aging. The present invention provides an improved wrinkle treatment.

SUMMARY OF THE PREFERRED EMBODIMENTS

In accordance with a first aspect of the present invention there is provided a method of preparing a skin treatment that includes preparing an extract of *Arnica montana* by mixing *Arnica montana* with ethyl alcohol, and filtering out the solids thereby resulting in liquid *Arnica montana* extract. In a first dilution, diluting the liquid *Arnica montana* extract with distilled water resulting in a first diluted *Arnica montana* extract. In a second dilution, diluting the first diluted *Arnica montana* extract with alkaline water resulting in a liquid skin treatment. In a preferred embodiment, a viscosity enhancer is added to the liquid skin treatment. Preferably, the alkaline water has a pH 8-10 and the first diluted *Arnica montana* extract:alkaline water ratio is less than 1:5. In a preferred embodiment,
the source of ethyl alcohol is 200 proof ethyl alcohol.

In accordance with another aspect of the present invention there is provided a skin treatment composition that includes an extract of *Arnica montana* including sesquiterpene lactones, distilled water, and alkaline water. In a preferred embodiment, the composition includes no more than 6 ppmw of sesquiterpene lactones. In a preferred embodiment, the composition includes an essential oil or colorant and a fragrance.

U.S. Patent Publication No. 2009/0041875 is incorporated herein by reference in its entirety.

BRIEF DESCRIPTION OF THE DRAWINGS

FIG. 1 is a sample mass-balance chart in accordance with a preferred embodiment of the present invention.

Like numerals refer to like parts throughout the several views of the drawings.

DETAILED DESCRIPTION OF THE PREFERRED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the FIGURES. It should be understood that any orientation of the components described herein is within the scope of the present invention.

Referring now to the drawings, wherein the showings are for purposes of illustrating the present invention and not for purposes of limiting the same, FIGS. 1-_ show a charging stand in accordance with a preferred embodiment of the present invention.

In one embodiment of the present invention, in general from 30 to 60 grams, and preferably from 40 to 45 grams, and most preferably 42 grams of *Arnica montana* are added to an aqueous ethanol solution of (a) from 1800 to 2400 grams, and preferably 2000 to 2200 grams, and most preferably 2173.5 grams. The aqueous ethyl alcohol has a water content close to the ethanol-water azeotrope, comprising a water concentration of about 5 wt %, more preferably 4.5 wt %, and most preferably the known, exact azeotropic water concentration of 4.37 wt %. After mixing over a predetermined time period at room temperature, the solids are filtered out and the extract is diluted with 1700 to 2100 grams of distilled water, preferably 1850 to 1950 grams of distilled water, and most preferably 1900 gram of distilled water. The extract/distilled water mixture is further diluted using from 3200 to 3700 grams of alkaline water, preferably 3400 to 3500 grams of alkaline water, and most preferably 3494 grams of alkaline water. Alkaline water is water that has been subjected to a process such as an electrolysis process that raises the pH of the water to from 7.5 to 10, preferably from 8.5 to 9.5, by making it rich in alkalizing compounds, such as calcium, silica, potassium, magnesium, and bicarbonate.

The final mixture may be used as is or further improved with excipients such as fillers, colorants and scents. These additives may include compounds that slightly increase the viscosity of the mixture such as hydroxypropyl methylcellulose (HPMC) which is also known in the trade as "Hypromellose". For example, the addition of 1 wt % HPMC increases the viscosity of the mixture to between 4-5 cp while the addition of 2 wt % gives a viscosity of 6-7 cp. The higher viscosity is desired for the look and feel of the mixture when used on the skin. As an alternative to Hypromellose, Natrosol 250 CS hydroxyethylcellulose by Ashland and/or the like can be used as a viscosity enhancer. Skin compatible colorants may be added to the mixture to enhance the aesthetic appeal of the product. An example is FD&C liquid green dye concentrate. When added to the mixture at a concentration of 6000 pmm by weight, the mixture takes on a very pleasing and soothing green hue. Other colorants can be used without limitation other than a requirement that they are not transferrable to the skin when the product is used. The aesthetics of the product may also be enhanced by the addition of one or more of the many dozens of scents that might be chosen by one skilled in the art. For example, the addition of a water-soluble fragrance concentrate at a level of 0.5-1.5 wt % usually yields a mixture with a very pleasing odor.

In a preferred embodiment, 42 g of *Arnica montana* (flowers, leaves, and stems) is contacted with a mixture comprising 2173.5 g ethyl alcohol and 102.4 g distilled water. This mixture is very close to the ethanol-water azeotrope. The composition is often cited as 95 wt % ethanol, more exactly as 95.5 wt % ethanol, and precisely as 95.63 wt % ethanol. The mixture is stirred slowly, shaken or rolled, preferably continuously, for generally 2 to 4 days and preferably 2 to 2.5 days.

The extract is tested analytically to verify the amount of dissolved solids. A small volume (10-20 mL) of the extract is filtered through a 0.2 µm polypropylene syringe filter and a known mass of the filtered liquid (15-20 grams) is weighed into a small aluminum pan using an analytical balance. The exact mass of the liquid sample is recorded and the sample is dried, first at 50° C. in a oven until the liquid has visually evaporated and then at 60-70° C. under vacuum for 0.5-1 hour. The mass of dry residue, which is the *Arnica* extract, is then determined from the final weight of the sample on the analytical balance. The liquid mixture so prepared should contain between 10-20 ppmw of *Arnica* extract, the variability being due primarily to variations in the samples of dried *Arnica* used. Although those skilled in the art will recognize that higher concentrations of extract in the final mixture can be easily adjusted to 10 ppmw by dilution, it has been found that dilution to a constant value is unnecessary for obtaining consistent performance of the extract on skin so long as the extract concentration remains in the 10-20 ppmw range.

The alcohol-water mixture, now containing extracts from the *Arnica montana*, is passed through a filter media having pore sizes of 100-150 µm or smaller. The filter can be selected from woven or nonwoven media, microporous media of various sorts, from plastic filter sieves made for such purposes, or from a variety of other small pore filter materials known in the art. Filter aids, such as diatomaceous earth, can be used but have found to be unnecessary to obtaining an excellent product. The filtered mixture is diluted with 1900 g of distilled water and 3494 g of potable alkaline water having a pH=9.5. To this diluted solution are added 191.8 g of Natrosol 250 CS LV hydroxypropyl methylcellulose (Dow Chemical), 0.43 g of fully soluble cosmetic grade FD&C liquid green colorant concentrate, and 76.7 g of Tea Tree Mint, a fully soluble scent compound (Wellington Fragrance Company, Livonia, Mich.). The completed solution is then bottled for use.

In arriving at the extraction composition, a number of other extractants were prepared and tested including pure ethanol, pure water and mixtures comprising 60% ABV (51.96 wt % ethanol) and 40% ABV (33.26 wt % ethanol). Also tested were dilutions using distilled water only as well as dilutions using a combination of distilled water and alkaline water. These extracts were tested on the skin by a select group of female and male adult volunteers who received the test extracts without any composition knowledge. The testers ranked, on a scale of 1-5 (best) the effectiveness and skin safety of the extracts in 12 categories: better texture, smaller pores, more glow, more softness, more firmness, more clean, less furrows, fewer age spots, less puffiness, less dark circles, less fine lines, and less blemishes. Unexpectedly, the extract obtained using the ethanol-water azeotrope outperformed all other extracts—a result that is impossible to predict even for one "skilled-in-the-art". Thus the test subjects reported a previously unreported, currently inexplicable, but profound synergy when the azeotropic extract was diluted with alkaline water in lieu of distilled water or tap water.

Fourier Transform Infrared Spectroscopy (FTIR) was used to obtain spectra that allowed the identification of some of the classes of compounds present in the extracts. When pure ethanol was used, the extracts contained very little of the sesquiterpene lactones, like Helenalin, which are known components of *Arnica*. As water was added to the extraction solvent, the FTIR peak associated with the lactone increased. It was clear from comparing the FTIR spectra that the composition of the extract changed and depended entirely on the ethanol/water ratio of the extract.

Sesquiterpene lactones, at "low" concentrations, are described in the literature as having anti-inflammatory, analgesic, and antiseptic properties. At "high" concentrations, however, Helenalin and its isomers are known to be cytotoxic and are claimed to be have used homeopathically to cause abortions. High concentrations of the extract also exhibit high allergy sensitizing capacity. At this time, the definitions of "low" and "high" are not well established. The concentration of all sesquiterpene lactone (SL) isomers, taken together in the final mixture, is expected to remain below about 6 ppmw based on extracted solids measurements and dilution ratios. This value is based on the premise that all extracted solids are sesquiterpene lactones and this is clearly not the case. Nevertheless, the assumption allows us to establish 6 ppmw as an upper limit for the SL concentration in the final product.

In yet another preferred embodiment of the invention, an extract of *Arnica montana* is obtained via the use of an ethanol-water azeotropic composition that optimizes the concentration of extracted actives suitable for skin care. More preferably this composition includes a non-zero but not maximum concentration of extracted sesquiterpene lactones, like Helenalin and its isomers. More preferably, a composition is provided that comprises the extract combined with alkaline water of pH 8-10 in a ratio of extract:alkaline water of less than 1:5, preferably less than 1:2, and most preferably 1.1:1-0.9:1.

The final mixture, a skin renewing astringent ready for use provides cleaner, firmer, brighter and smoother skin, improved texture, smaller pores, and in addition eye bags, dark circles, brow furrow, smile and fine lines, scars and sun damaged skin are all preferably reduced along with an overall younger-looking appearance. Unexpected results include improving cystic acne and breaks-out in general, reduction in hyperpigmentation, reduction in skin fat deposits, soothing rashes and insect bites. It also smooths and tightens cellulite. Thus it can be used also as a cellulite gel or eye, face, neck and throat cream.

A sample mass-balance chart is shown in FIG. 1.

Another embodiment of the present invention involves treating skin with an alcohol extract of *Arnica* or derivatives thereof to reduce wrinkles and provide other cosmetic benefits. Preferably the *Arnica* extract is extracted from *Arnica* with alcohol. In a preferred embodiment, mineral water (or sparkling mineral water) is added to the alcohol *Arnica* extract.

In a preferred embodiment, the invention includes an extract of dry *Arnica* leaves and flowers, ethyl alcohol and mineral water. It will be appreciated that other alcohols can be used. In an exemplary preferred embodiment, *Arnica* from Tadin Herb & Tea Company in Los Angeles can be used. However, this is not a limitation on the present invention.

In an example of a preferred preparation of the invention, about 1 to about 10 ounces, preferably of dry *Arnica* is mixed with about 1.75 to about 19 liters (or about 5 gallons), preferably of a liquid including ethyl alcohol in a glass jar. It will be appreciated that larger or smaller batches can made as long as the relative ratios are similar. For example, about 1-2 ounces of *Arnica* can be mixed with about 1.75 liters of the alcohol liquid. Glass is used so not to absorb plastic and other chemicals. However, other materials, such as plastic can be used. A lid is placed on the jar and the sealed container is preferably placed in a cool (e.g., about 65° F. to about 78° F.), dark environment (e.g., a cabinet) for approximately 3-4 weeks. Below 65° F. is also acceptable. However, this is not a limitation and the container with the contents therein can be stored in a non-dark, lighted area and/or heated area.

Preferably, the jar and its contents is shaken and/or stirred every approximately 2-3 days and then returned to the dark environment. After approximately 3-4 weeks, the liquid is strained from the *Arnica*, thereby providing an active alcohol *Arnica* extract. For example, the straining can be done by a strainer and cheese cloth. In a preferred embodiment, the cheese cloth is then wrapped around the wet *Arnica* to squeeze out the liquid absorbed by the *Arnica*.

In a preferred embodiment, approximately 10 ounces of mineral water is mixed with approximately 60 ounces of the strained liquid. In another preferred embodiment, between about 3 mL and about 6 mL of essential oil is mixed into the *Arnica* extract/mineral water product. For example, essential oils such as peppermint, lemon, orange, grapefruit, lime, tea tree, *eucalyptus*, lavender, rose, frankincense, cypress, clove, tangerine, spearmint, wintergreen, oregano, rosemary and geranium can be used. It will be appreciated that one or more of the essential oils can be used. In another embodiment, the essential oil(s) can be omitted. In a more preferred embodiment, the invention is a mixture consisting of a liquid alcohol extract of *Arnica* mixed with mineral water and an essential oil (or one or more essential oils).

The mixture is then placed into a container, such as a sterilized dark colored jar and labeled. Preferably, the resulting mixture is a clear, amber colored liquid with a mild smell by itself. In other embodiments the resulting mixture can be another color. Essential oils may add additional healing benefit and natural fragrance. The invention can also be formatted in a cream, gel, etc. The invention can also be administered using roll on, sprays, and pumps to apply the product.

In other embodiments, the mixture can include fractionated coconut oil, jojoba oil, or mineral oil, rose water and/or distilled water. If necessary, an emulsifier can be added.

After cleaning the skin, a cotton pad or similar item is used to distribute the product on face, neck, chest, and hands (or other locations) if desired twice daily. It is recommended to let dry 3-5 minutes before applying any other product. Besides a wrinkle treatment, the invention can also work on minor burns, rashes, arthritis, etc.

It will be appreciated that the invention is used on exposed skin to provide a more youthful appearance. The invention preferably improves deep furrows and lines on the brows, smile and neck creases along with brightening, retexturing and tightening the skin. Bags and dark circles under eyes can also be improved and wrinkles on eye lids can be diminished. The invention can also help reduce age/sun spots on face, hands, arms and other areas exposed to the sun.

In a preferred embodiment, the product is stored in glass containers so not to absorb chemicals from plastic, metal or wood containers and is kept out of sunlight and heat. In a preferred embodiment, the final product is packaged in dark colored glass containers preferably with a pump so the product is not contaminated by constant opening.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers or dimensions noted herein are only examples: alternative implementations may employ differing values, measurements, dimensions or ranges.

The teachings of the disclosure provided herein can be applied to other systems, not necessarily the system described above. The elements and acts of the various embodiments described above can be combined to provide further embodiments. Any measurements described or used herein are merely exemplary and not a limitation on the present invention. Other measurements can be used. Further, any specific materials noted herein are only examples: alternative implementations may employ differing materials.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of preparing a skin treatment, the method comprising:
   preparing an extract of *Arnica montana* by mixing *Arnica montana* with ethyl alcohol, and filtering out the solids thereby resulting in liquid *Arnica montana* extract;
   in a first dilution, diluting the liquid *Arnica Montana* extract with distilled water resulting in a first diluted *Arnica montana* extract; and
   in a second dilution, diluting the first diluted *Arnica montana* extract with alkaline water resulting in a liquid skin treatment.

2. The method of claim 1 wherein a viscosity enhancer is added to the liquid skin treatment.

3. The method of claim 1 wherein the alkaline water has a pH 8-10 and the first diluted *Arnica montana* extract: alkaline water ratio is less than 1:5.

4. The method of claim 1 wherein the ratio of the volume of distilled water to the liquid *Arnica montana* extract is greater than the ratio of the volume of alkaline water to the first diluted *Arnica montana* extract.

5. The method of claim 3 where the ratio is less than 1:2.

* * * * *